United States Patent
Lesko et al.

(10) Patent No.: US 10,285,847 B2
(45) Date of Patent: May 14, 2019

(54) OSTOMY POUCH WITH FILTERING SYSTEM

(75) Inventors: Marc Lesko, Jackson, NJ (US); Mingliang Lawrence Tsai, Holmdel, NJ (US); Gary Oberholtzer, Feasterville, PA (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 0 days.

(21) Appl. No.: 13/248,704

(22) Filed: Sep. 29, 2011

(65) Prior Publication Data

US 2013/0085463 A1   Apr. 4, 2013

(51) Int. Cl.
*A61F 5/441*  (2006.01)

(52) U.S. Cl.
CPC .................... *A61F 5/441* (2013.01)

(58) Field of Classification Search
USPC .......................................... 604/333
See application file for complete search history.

(56) References Cited

U.S. PATENT DOCUMENTS

| | | | |
|---|---|---|---|
| 4,411,659 A | 10/1983 | Jensen et al. | |
| 5,074,851 A | 12/1991 | Plass et al. | |
| 5,250,042 A | 10/1993 | Torgalkar et al. | |
| 5,306,264 A | 4/1994 | Ferguson et al. | |
| 5,401,264 A * | 3/1995 | Leise, Jr. ............... | A61F 5/441 604/333 |
| 5,643,234 A * | 7/1997 | Lesko ..................... | A61F 5/441 604/333 |
| 5,690,623 A | 11/1997 | Lenz et al. | |
| 7,083,569 B2 * | 8/2006 | Boulanger ............. | A61F 5/445 600/32 |
| 7,214,217 B2 * | 5/2007 | Pedersen ................ | A61F 5/441 604/332 |
| 7,476,220 B2 * | 1/2009 | Lillegaard .................... | 604/342 |
| 7,572,492 B2 * | 8/2009 | Bager et al. .................. | 428/35.2 |
| 7,604,622 B2 * | 10/2009 | Pedersen ................ | A61F 5/448 604/333 |
| 2003/0014023 A1 | 1/2003 | Kanbara | |
| 2003/0040727 A1 * | 2/2003 | Boulanger ............. | A61F 5/445 604/332 |
| 2005/0143696 A1 * | 6/2005 | Pedersen ................ | A61F 5/441 604/332 |
| 2007/0049880 A1 * | 3/2007 | Suehr ...................... | A61F 5/441 604/333 |

(Continued)

FOREIGN PATENT DOCUMENTS

| | | |
|---|---|---|
| CN | 103228236 A | 7/2013 |
| EP | 0443728 A2 | 8/1991 |

(Continued)

OTHER PUBLICATIONS

EP 11829957.7 Supplementary European Search Report Completed May 14, 2014.

(Continued)

*Primary Examiner* — Tatyana Zalukaeva
*Assistant Examiner* — Guy K Townsend
(74) *Attorney, Agent, or Firm* — Wilson Sonsini Goodrich & Rosati

(57) ABSTRACT

An ostomy appliance including an ostomy pouch with a filter and a center pleated panel to protect the filter, facilitate deodorization and deter ballooning.

9 Claims, 5 Drawing Sheets

(56) References Cited

U.S. PATENT DOCUMENTS

| | | | |
|---|---|---|---|
| 2007/0203466 A1* | 8/2007 | Pedersen | A61F 5/441 604/333 |
| 2008/0004580 A1 | 3/2008 | Mullejans et al. | |
| 2009/0227973 A1 | 9/2009 | Bjarne | |
| 2009/0247970 A1* | 10/2009 | Keleny | A61F 5/441 604/333 |
| 2010/0241092 A1* | 9/2010 | Nguyen-DeMary | A61F 5/4407 604/336 |
| 2012/0283678 A1* | 11/2012 | Nguyen-DeMary | A61F 5/445 604/337 |
| 2017/0042723 A1 | 2/2017 | Oberholtzer et al. | |

FOREIGN PATENT DOCUMENTS

| | | |
|---|---|---|
| EP | 3134040 A1 | 3/2017 |
| GB | 2149306 | 6/1985 |
| GB | 2116433 B | 8/1985 |
| GB | 2461721 | 1/2010 |
| JP | S6121414 B2 | 5/1986 |
| JP | 2000126216 A | 5/2000 |
| JP | 2001031115 A | 2/2001 |
| JP | 2003010226 A | 1/2003 |
| JP | 2003019154 A | 1/2003 |
| JP | 2003513776 A | 4/2003 |
| JP | 2005211178 A | 8/2005 |
| JP | 2010504150 A | 2/2010 |
| JP | 2011136574 A | 7/2011 |
| WO | WO-2015164832 | 10/2015 |

OTHER PUBLICATIONS

Chinese Patent Application No. 201180057593.X 4th Office Action dated Jun. 30, 2016.
Japanese Patent Application No. 2013-531905 Decision of Rejection dated May 10, 2016.
Australia Patent Application No. 2016266028 Examination Report No. 1 dated Sep. 12, 2017.
Japanese Patent Application No. 2016-177009 Office Action dated Jul. 25, 2017.
Canadian Patent Application No. 2,813,248 Office Action dated Oct. 23, 2017.
European Patent Application No. 15783238.7 extended European Search Report dated Nov. 23, 2017.
Canadian Patent Application No. 2,813,248 Office Action dated Jul. 10, 2018.
Chinese Patent Application No. 201580034580.9 Office Action dated Jul. 9, 2018.
Japanese Patent Application No. 2016-177009 Office Action dated Mar. 6, 2018.
Japanese Patent Application No. 2016-563963 Office Action dated Mar. 8, 2019.

* cited by examiner

OSTOMY POUCH WITH FILTERING SYSTEM

FIELD OF THE INVENTION

The present invention relates to ostomy appliances and more particularly to ostomy pouches having a filter.

BACKGROUND OF THE INVENTION

Gas management and odor removal is of very significant concern in ostomy appliances. Despite the advances in various filter designs, there is still a need by ostomates for improved filter performance. Most ostomy filters currently on the market only work for a short time, in many instances less then 1 day. The key complaints have been leakage, clogging which leads to ballooning, insufficient deodorization, and reduced wear time. When some marketed filters stop working there can be leakage of stool outside of the pouch from the filter. Most of filter designs now utilize an oleophobic membrane to protect the filter from leaking in the presence of the enzymes and chemicals from feces. However, commercial ostomy pouches with or without oleophobic membranes have not addressed the clogging issue as effectively as desired by many ostomates. There are also ostomy pouches utilizing multiple membranes to improve both oleophobic and hydrophobic property in the filter, but this design increases the resistance of air flow significantly.

Most commercial ostomy filters are based on radial flow in which the gases flow along the plane of a relatively flat filter rather than directly or axially through the thickness of the filter. Such a radial or planar flow type is used in order to increase the reaction time between gases and the activated carbon. An axial flow type filter is difficult to make because of the difficulties involved in balancing the deodorization efficiency, the air flow requirement, and the profile of the filter. It is, however, desirable to have an axial flow filter that would allow a relatively small filter to be used without sacrificing the deodorization performance. A small filter size is preferred because it allows the filter to be positioned as close as possible to the seam of a pouch so that the face of the filter is not directly in front of the opening of the stoma, thus decreasing the tendency of filter clogging.

Accordingly, there is a need for an improved filtering system to improve clogging resistance. Furthermore, there is a need for an axial flow filter in order to minimize the filter profile and to make a small size filter possible.

SUMMARY OF THE INVENTION

One aspect of the invention in the filter design of the present invention is to improve the clogging resistance by using the newly developed pleated center panel design. This design includes a filter in the front panel of the pouch and a center panel of film that is intended to shield the filter from direct exposure to stool that is expelled from the stoma. The center panel has at least one pleat, and preferably two pleats, that are intentionally formed into the center panel. These pleats allow the gas to travel from the stoma area into the filter area while preventing a majority of the stool from get to and fouling the filter. Without these pleats the center panel has a tendency to block or seal against the front panel of the pouch and not allow gas to get to the filter and thus cause ballooning of the pouch. Optionally, an open cell foam can be added between the face of the filter and the pleats to further reduce any stool that might get past the pleats.

Another aspect of the invention is the incorporation of a filter designed for axial air flow. The pleated design makes possible the use of a small size filter which has a low profile. Both the strip filter and axially flow filter can be combined with the pleated center panel design to improve the clogging resistance.

Another aspect of the invention is a strip filter design, in which the filter is wrapped with an odor barrier film around its perimeter. Such a design allows the filter to maximize its deodorization performance without significantly increasing the air flow resistance.

A test method was devised to mimic actual usage of filtered pouches and their resistance to clogging. Testing was conducted on a specifically designed tilting table test rig. The test rig was designed to hold the test filtered pouches in the vertical position and tilt them to the horizontal position at timed intervals. The tilt table test rig also incorporates a means to inject air into the filtered test pouch to simulate gas produced by the body. The test pouches with filters are also filled with a simulated stool referred to as Feclone, which is commercially sold and mixed to a desired viscosity of 1 part solid to 3 parts water, to challenge the filtering system from a clogging perspective. When the testing is conducted, the filtering system is exposed to the simulated stool and simulated gas at timed intervals of 10 minutes in each position. Pouches are continuously cycled through the vertical and horizontal positions during this tilt table test. During each cycle the test pouches are injected with about 300 cc air to fill each pouch every 10 minutes with a fill time of 5 seconds. When the filter is not clogged, the test pouch deflates normally by releasing the air through the filter system. Testing is continued until all pouches have failed to release air from inside of the pouch, as indicated by the ballooning in the pouch. The criteria for filter failure is when a test filtered pouch fails to deflate and stays fully ballooned for 3 consecutive tilt table cycles. When ballooning occurs, the simulated stool clogs the filter and the filter system can no longer release the air.

Numerous commercial filtering systems were evaluated. Results of various pouch designs, with and without pleats, are summarized in FIG. 1. Testing showed that the center pleated panel filtering system doubled the life of the filter to around 300 minutes, which is defined by the time that the filter becomes clogged. Testing also showed that the pleated center panel filtering system when used with the foam tripled the life of the filter to around 600 minutes. Results of various pouch designs, with and without pleats, are summarized in FIG. 1. Clogging resistance was also compared with and without the foam in the filter system.

The physical dimension of an axial flow filter versus a radial flow filter is shown in Table 1. Table 2 is a summary of the $H_2S$ deodorization results of the same axial flow filter and the radial flow filter at various relative humidity and with different carrier gases. FIG. 2 is a graph of the results from Table 2. As can be shown from Table 2 and FIG. 2, an axially flow filter outperformed the radial flow filter in the $H_2S$ deodorization even though the activated carbon layer is thinner and the surface area is smaller.

TABLE 1

Physical Dimension of an Axial Flow Filter versus a Radial Flow Filter

|  | Radial Flow Filter (Freudenberg Improved Option 20 w/o ePTFE membrane), activated carbon thickness | Axial Flow Filter (Donaldson Nicom 39 with an ePTFE membrane) |
|---|---|---|
| Activated Carbon thickness, mm | 2.2 mm | 1.1 mm |
| Activated Carbon surface area, mm$^2$ | 484 | 270 |

TABLE 2

$H_2S$ Deodorization Breakthrough Time and Back Pressure

| | Radial Flow Filter (Freudenberg Improved Option 20 w/o ePTFE membrane), activated carbon thickness | | Axial Flow Filter (Donaldson Nicom 39 with an ePTFE membrane) | |
|---|---|---|---|---|
| %RH and Carrier Gas | $H_2S$ Deodorization Time, minutes | Back Pressure, mbar | $H_2S$ Deodorization Time, minutes | Back Pressure, mbar |
| 0%/$CH_4$ and $N_2$ | 120-150 | ~1 | 25-50 | ~10 |
| 0%/Air | 40 | ~1 | N/A | ~10 |
| 5-7%/Air, | 170 @ 7% RH | ~1 | 552 @ 5% RH | ~10 |
| 35%/Air, | 580 | ~1 | 1500-2790 | ~10 |
| 35%/$CH_4$ and $N_2$ | 320-483 | ~1 | 270 | ~10 |
| 35%/Air | 700-880 | ~1 | 2353 | ~10 |
| 50%/Air | 960-1240 | ~1 | 3090 | ~10 |
| 80%/Air | 1960 | ~1 | 3940 | ~10 |

Table 3 is a summary of the $H_2S$ deodorization results of a strip filter, in a rectangular dimension 15 mm×33 mm, versus a round filter with a diameter of 25.4 mm. Although the total surface area and the activated carbon thickness are about the same, the strip filter had significantly higher deodorization time due to the increased effective flow distance. In this example, the effective flow distance is almost 33% longer, resulting in a longer $H_2S$ deodorization time.

TABLE 3

$H_2S$ Deodorization of a Strip Filter versus a Round Filter

| | Strip Filter (Freudenberg Improved Option 20) | Round Filter (Freudenberg Improved Option 20) |
|---|---|---|
| Activated Carbon thickness, mm | 2.2 mm | 2.2 mm |
| Activated Carbon surface area, mm$^2$ | 495 | 484 |
| Effective Flow Distance | 16 mm | 12 mm |
| $H_2S$ Deodorization Time, minutes (0%/$CH_4$ and $N_2$) | 138 | 108 |
| Back Pressure, mbar | 3.1 | 1.0 |

The present invention includes the following:
1. Pleated center panel that improves clogging resistance. An open cell foam can be added to further increase clogging resistance. This pleated design, with and without the foam, can be used with all types of filters, round or strip, radial flow or axial flow. The pleated design, with and without the foam, can be used in either drainable or closed pouch.
2. An axial flow filter with an equivalent or better deodorization time although the activated carbon layer is thinner and the surface area is smaller in an axial flow filter.
3. A strip filter with an equivalent or better deodorization time as a result of the increased effective flow distance, as compared to a round filter which has the about the same thickness and surface area.

DETAILED DESCRIPTION OF THE DRAWINGS

Figure 1:
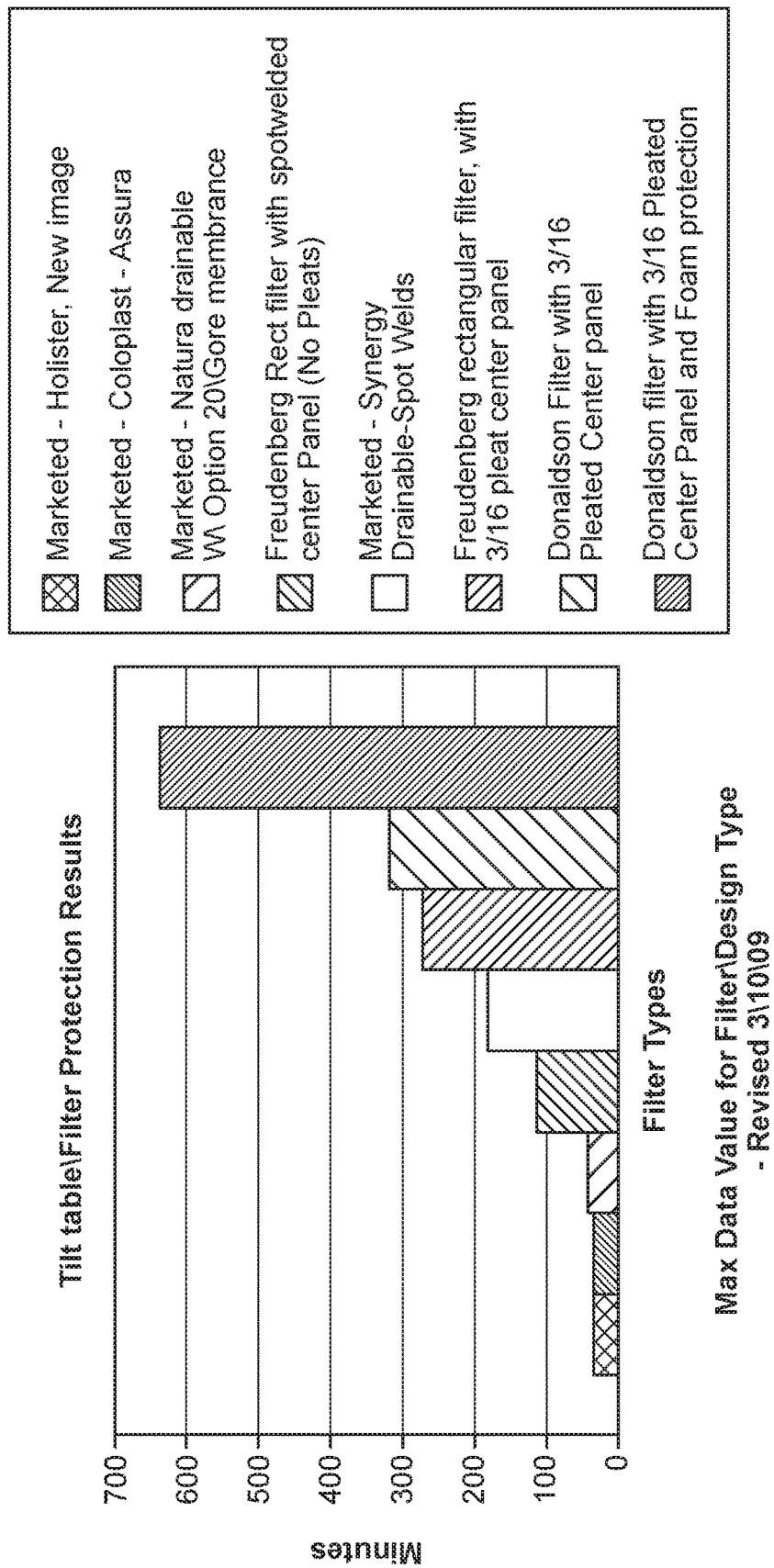
FIG. 1 is a graph of the life of filter defined by time to clog as tested by tilt table.
Figure 2:
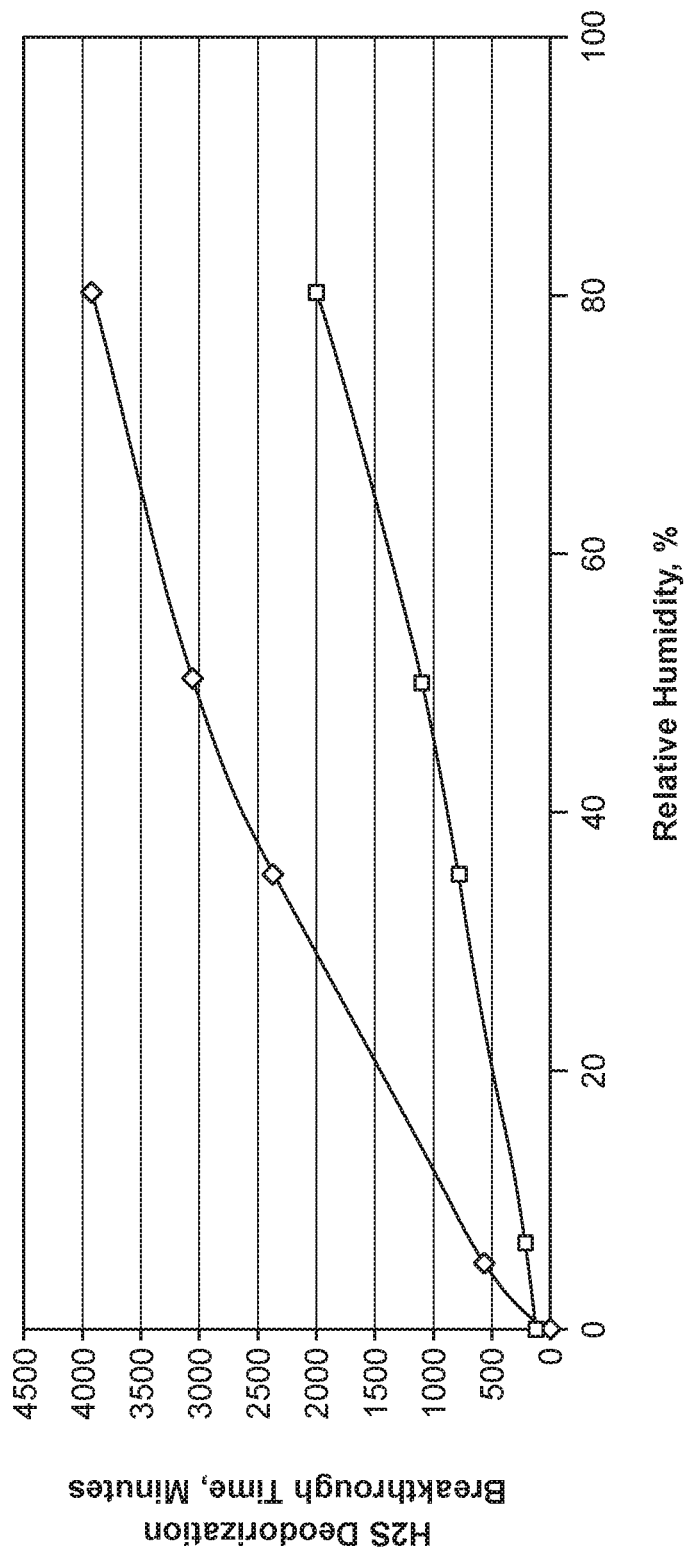
FIG. 2 is a graph of the effect of relative humidity on $H_2S$ deodorization breakthrough time in air.
Figure 3:
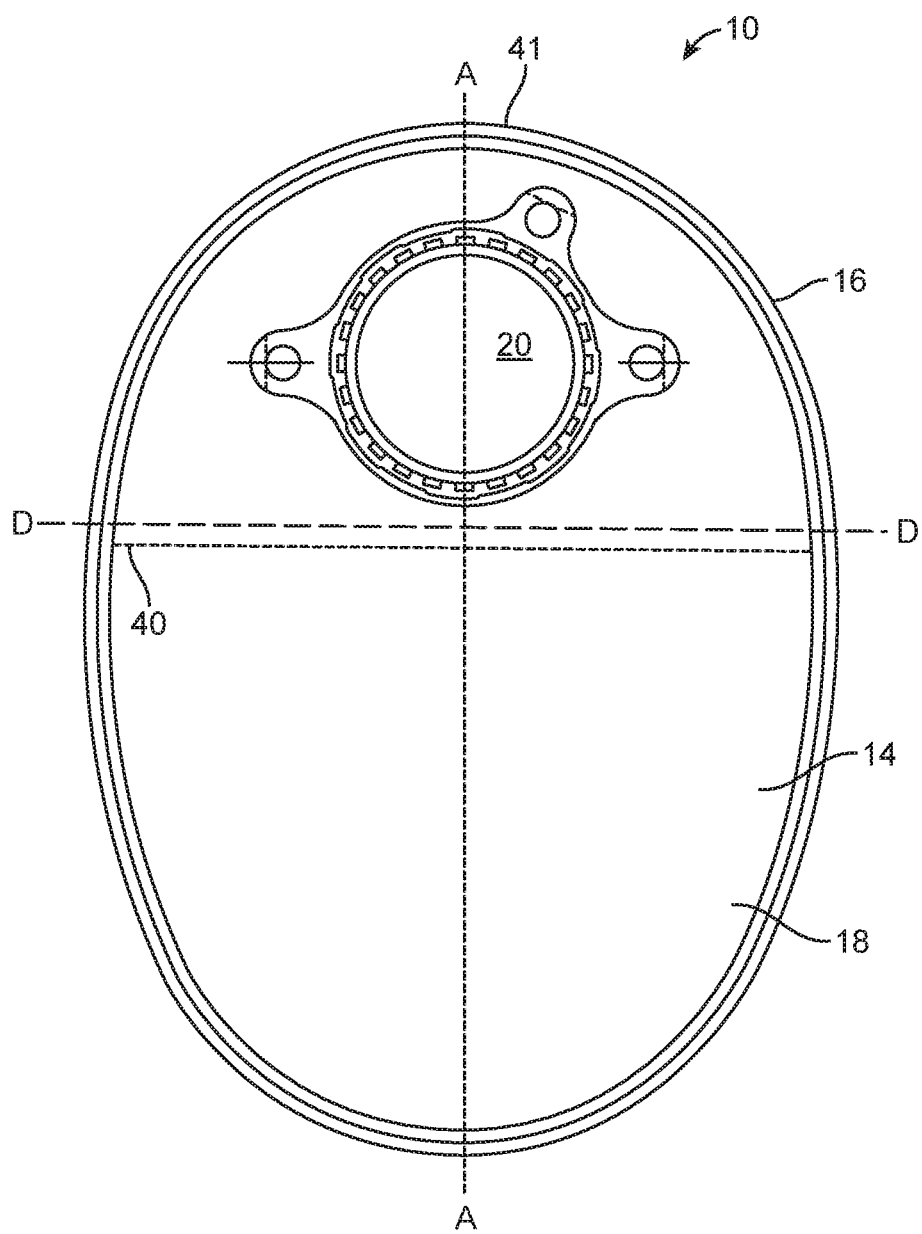
FIG. 3 is a rear elevational view of an ostomy appliance in accordance with the present invention.
Figure 4:
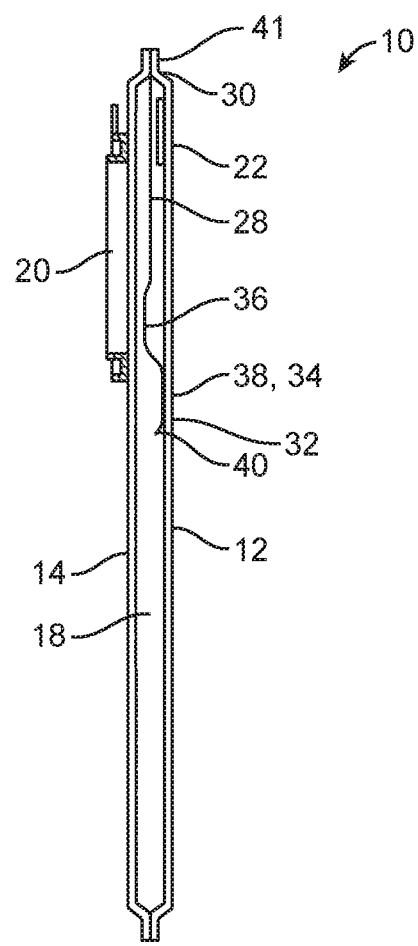
FIG. 4 is a cross-sectional view along line A-A of FIG. 3.
Figure 5:
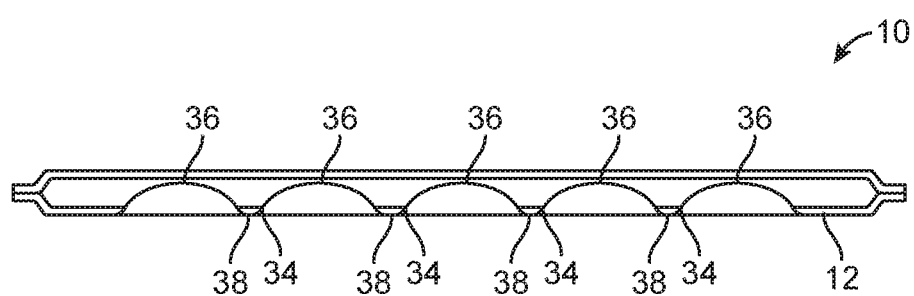
FIG. 5 is a cross-sectional view along line D-D of FIG. 3 (without the stomal flange and filter, for clarity).
Figure 6:
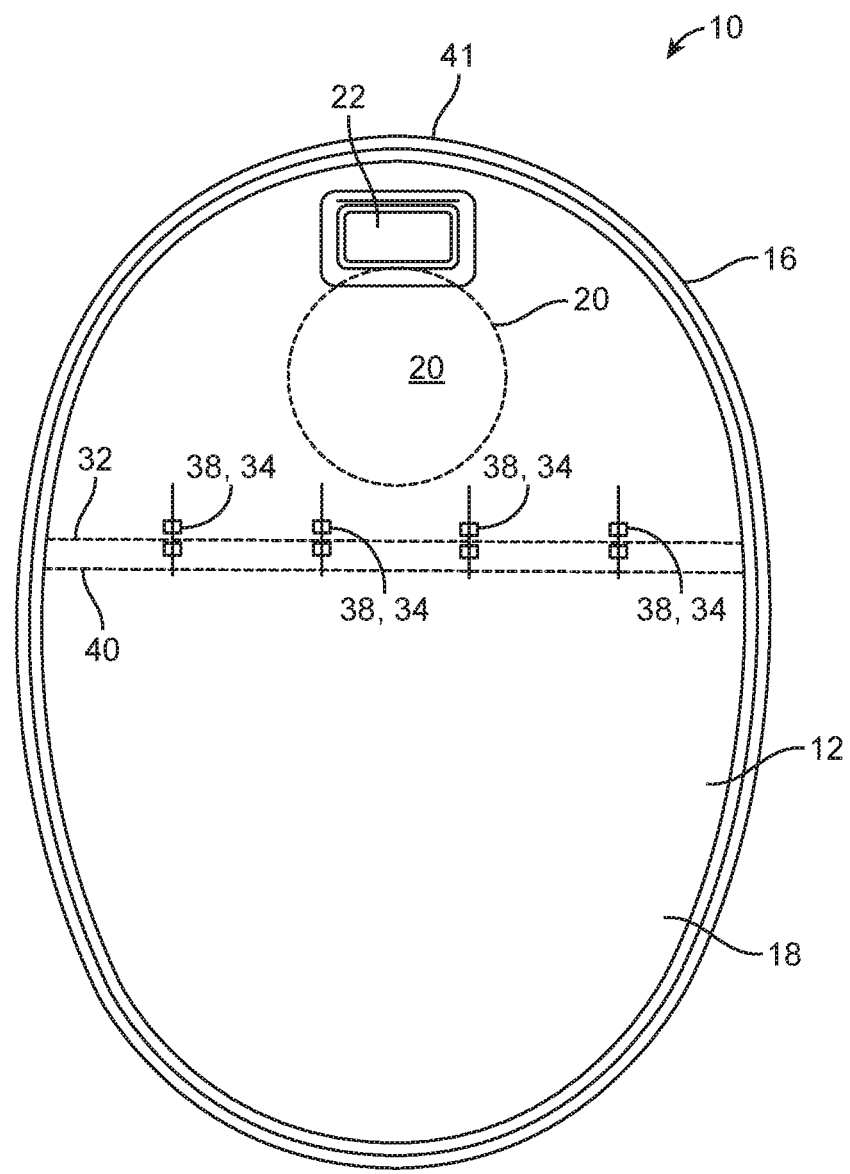
FIG. 6 is a front elevational view of the ostomy appliance of FIG. 3 (without the stomal flange, for clarity).

The present invention is an ostomy appliance 10 (FIGS. 3-6) having a front panel 12 and rear panel 14 that are sealed together around the peripheries of the panels to form the outer edge 16 of a closed ostomy pouch 18. The rear panel 14 includes a stomal opening 20 through which body waste is excreted when the ostomy pouch is appropriately placed on a body with the stomal opening 20 surrounding the stoma. The ostomy pouch 18 includes a filter assembly 22 attached to the front panel 12 typically by welding. The rear panel 14 includes an opening for permitting and facilitating the passage of the body waste odor deodorized by the filter assembly 22 to the atmosphere.

The ostomy pouch 18 further includes a center pleated panel 28 present between the front panel 12 and rear panel 14. This center pleated panel 28 includes an edge 30 attached to the outer edge 16 of the ostomy pouch 18. The center pleated panel has a partially free edge portion 32 that is attached intermittently 34 to the inner surface of the front panel 12. This center pleated panel 28 is predeterminedly dimensioned and attached to the front panel 12 in a manner to produce extra material in the form of folds, corrugations or pleats 36 within the pouch 18; the pleats 36 permit odorous gas to reach the filter assembly 22 for deodorization while deterring a ballooning of the pouch 18 due to captured gas within the pouch.

The pleated center panel 28 extends partially down from the top 36 of the ostomy pouch so as to at least partially and preferably totally cover and protect the filter assembly 22 from any body waste material entering the pouch 18 through the stomal opening 20. The pleats 36 are formed in part by the spot welds 38 securing the edge portion 32 to the front panel 12. The pleated center panel 28 has a bottom edge 40. The pleated center panel 28 is preferably made of the same standard ostomy pouch material used for the front panel 12 and rear panel 14.

Variations and modifications to the preferred embodiment may be made while falling within the scope of the invention as defined by the claims.

What is claimed:
1. An ostomy appliance comprising:
two opposing panels comprising a front panel and a rear panel, the two opposing panels at least partly sealed to one another along their peripheries to form an outer edge of the ostomy appliance, the panels forming a pouch for capturing body waste, the rear panel having a stomal opening for positioning around a stoma so that body waste excreted through the stomal opening is captured in the pouch, the pouch having a filter attached to the front panel, the filter capable of deodorization of odorous gas from body waste and emitting deodorized gas to an atmosphere through the filter, and a center panel between the two opposing panels, wherein the center panel comprises a top edge attached to the outer edge of the ostomy appliance and a bottom edge intermittently attached to the front panel to form at least one corrugation, fold or pleat within the pouch, wherein the at least one corrugation, fold or pleat is capable of preventing sealing of the center panel against the front panel;

the at least one corrugation, fold or pleat configured to deter ballooning of the pouch from gas buildup, and wherein the center panel completely covers the filter for protecting the filter from body waste material excreted from the stomal opening into the pouch.

2. The ostomy appliance of claim 1 wherein the center panel is suitably folded to maintain openings for facilitating passing of gas to the filter.

3. The ostomy appliance of claim 1 further including an open cell foam between the filter and the center panel.

4. The ostomy appliance of claim 1 wherein the filter is an axial flow type of filter or strip filter.

5. The ostomy appliance of claim 1 wherein the filter is a strip filter.

6. The ostomy appliance of claim 5, wherein the strip filter is wrapped with an odor barrier film around its perimeter.

7. An ostomy pouch comprising:
   a front panel comprising a deodorizing filter assembly attached to the front panel;
   a rear panel comprising a stomal opening; and
   a center panel positioned between the front panel and rear panel, the center panel comprising:
   a top edge attached to an outer edge of the ostomy pouch, and a bottom edge attached intermittently to the front panel to form at least one corrugation, fold or pleat within the ostomy pouch, wherein the at least one corrugation, fold or pleat is capable of preventing sealing of the center panel against the front panel;
   wherein the center panel covers or shields the filter assembly from body waste material excreted from the stomal opening into the ostomy pouch.

8. The ostomy pouch of claim 7, wherein the center panel is attached to an outer edge of the ostomy pouch.

9. The ostomy appliance of claim 1, wherein the center panel comprises a curved edge, including the top edge, attached to the outer edge and the bottom edge comprises the diameter of the center panel.

* * * * *